(12) United States Patent
Ailawadi et al.

(10) Patent No.: US 11,937,848 B2
(45) Date of Patent: Mar. 26, 2024

(54) PORT APPARATUS AND SHEATH DEVICE FOR ELECTROCAUTERY AND RELATED METHODS THEREOF

(71) Applicant: University of Virginia Patent Foundation, Charlottesville, VA (US)

(72) Inventors: Gorav Ailawadi, Charlottesville, VA (US); James Hunter Mehaffey, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 1307 days.

(21) Appl. No.: 16/308,039

(22) PCT Filed: Jun. 9, 2017

(86) PCT No.: PCT/US2017/036741
§ 371 (c)(1),
(2) Date: Dec. 7, 2018

(87) PCT Pub. No.: WO2017/214496
PCT Pub. Date: Dec. 14, 2017

(65) Prior Publication Data
US 2019/0307488 A1    Oct. 10, 2019

Related U.S. Application Data

(60) Provisional application No. 62/348,535, filed on Jun. 10, 2016.

(51) Int. Cl.
*A61B 17/34* (2006.01)
*A61B 17/32* (2006.01)
(Continued)

(52) U.S. Cl.
CPC .......... *A61B 17/3476* (2013.01); *A61B 17/32* (2013.01); *A61B 17/34* (2013.01);
(Continued)

(58) Field of Classification Search
CPC ............ A61B 17/3439; A61B 17/3476; A61B 18/1487
See application file for complete search history.

(56) References Cited

U.S. PATENT DOCUMENTS 4,691,703 A     9/1987  Auth et al.
5,183,464 A *   2/1993  Dubrul .............. A61M 25/0662
                                                 606/198

(Continued)

FOREIGN PATENT DOCUMENTS

EP       2316360        5/2011
WO    WO 2016/127178    8/2016

OTHER PUBLICATIONS

Bovie Medical, "3 Key Differences Between Electrosurgery & Electrocautery", Bovie Medical Insights, Jan. 20, 2015, 3 pages, Bovie Medical Corporation.

(Continued)

*Primary Examiner* — Nicholas W Woodall
(74) *Attorney, Agent, or Firm* — Robert J. Decker (57) ABSTRACT

A method and apparatus for performing electrocautery on a site of a subject that includes inserting a trocar device into the location of the site of the subject and electro-cauterizing the site of the subject using a diode included with the trocar device. A method and apparatus for performing electrocautery on a site of a subject that includes inserting one or more medical tubes or medical instruments or devices that extends through an expandable sheath; and electro-cauterizing the site of the subject using a diode included with the expandable sheath device.

3 Claims, 9 Drawing Sheets

(51) Int. Cl.
  *A61B 18/00* (2006.01)
  *A61B 18/08* (2006.01)
  *A61B 18/12* (2006.01)
  *A61B 18/14* (2006.01)
  *C09K 19/02* (2006.01)
  *C09K 19/38* (2006.01)
  *F03G 7/06* (2006.01)
  *G06F 3/01* (2006.01)
  *A61B 1/00* (2006.01)
  *A61B 1/313* (2006.01)
  *A61B 17/02* (2006.01)

(52) U.S. Cl.
  CPC .......... *A61B 17/3423* (2013.01); *A61B 18/00* (2013.01); *A61B 18/08* (2013.01); *A61B 18/12* (2013.01); *A61B 18/1487* (2013.01); *C09K 19/0208* (2013.01); *C09K 19/38* (2013.01); *F03G 7/0614* (2021.08); *F03G 7/065* (2013.01); *G06F 3/016* (2013.01); *A61B 1/00154* (2013.01); *A61B 1/3132* (2013.01); *A61B 17/0218* (2013.01); *A61B 2017/3405* (2013.01); *A61B 17/3415* (2013.01); *A61B 17/3474* (2013.01); *A61B 2018/00589* (2013.01); *A61B 2018/00595* (2013.01); *A61B 2018/00601* (2013.01); *C09K 2219/03* (2013.01)

(56) References Cited

U.S. PATENT DOCUMENTS

| | | | |
|---|---|---|---|
| 5,221,281 A * | 6/1993 | Klicek | A61B 18/1487 606/45 |
| 5,387,197 A | 2/1995 | Smith et al. | |
| 5,658,279 A | 8/1997 | Nardella et al. | |
| 5,718,703 A | 2/1998 | Chin | |
| 5,776,126 A | 7/1998 | Wilk et al. | |
| 5,830,214 A | 11/1998 | Flom et al. | |
| 5,925,041 A | 7/1999 | Long et al. | |
| 6,187,002 B1 | 2/2001 | Long et al. | |
| 6,254,622 B1 | 7/2001 | Hood | |
| 6,280,450 B1 | 8/2001 | McGuckin, Jr. | |
| 6,451,017 B1 | 9/2002 | Moutafis et al. | |
| 7,604,648 B2 | 10/2009 | Kerr | |
| 8,506,565 B2 * | 8/2013 | DeCarlo | A61B 18/1402 606/45 |
| 8,764,765 B2 | 7/2014 | Piskun et al. | |
| 9,125,573 B2 | 9/2015 | Koyrakh et al. | |
| 2005/0182454 A1 | 8/2005 | Gharib et al. | |
| 2008/0242939 A1 | 10/2008 | Johnston | |
| 2016/0228176 A1 | 8/2016 | Colquhoun | |
| 2017/0164977 A1 * | 6/2017 | Griffiths | B03C 3/38 |

OTHER PUBLICATIONS

Cordero, Ismael, "Electrosurgical units—how they work and how to use them safely", Community Eye Health Journal, 2015, pp. 15-16, vol. 28, No. 9.

* cited by examiner

PORT APPARATUS AND SHEATH DEVICE FOR ELECTROCAUTERY AND RELATED METHODS THEREOF

RELATED APPLICATIONS

The present application is a national stage filing of International Application No. PCT/US2017/036741, filed Jun. 9, 2017 which claims benefit of priority under 35 U.S.C § 119 (e) from U.S. Provisional Application Ser. No. 62/348,535, filed Jun. 10, 2016, entitled "Laparoscopic and Thoracoscopic Port Device For Cauterizing and Related Method Thereof"; the disclosures of which are hereby incorporated by reference herein in their entirety.

FIELD OF INVENTION

The present disclosure relates generally to electrocautery devices and, more particularly, electrocautery devices integrated with one or more medical devices or instruments to control bleeding associated with surgery.

BACKGROUND

Many surgical operations are performed minimally invasively through small circular plastic or metal ports enabling instruments to reach organs from outside the skin.

When ports are removed, small vessels in the chest or abdominal wall can bleed which can be difficult to fix.

Electrocautery devices are commonly used in a variety of surgical operations to control bleeding from tissue and organs. Electrocautery devices may typically include a conducting element configured to deliver high-frequency current to tissues sufficient to generate intracellular heat, tissue desiccation and/or protein denaturation. In this manner, electrocautery devices may be configured to cauterize tissues and small vessels, thereby achieving hemostasis. Suction devices may be used in conjunction with electrocautery devices to draw blood away from tissues to allow the target bleeding site to be located and cauterized. Suction may also be used as an adjunct to cautery inasmuch as flowing blood can overwhelm the effectiveness of cautery. Moreover, laparoscopic or thoracoscopic port devices may also be used for procedures also requiring electrocautery devices.

In electrosurgical procedures, the tissue may be heated by an electric current. Electrical devices that create a heated probe may be used for the cauterization of tissue in some applications.

Electrocautery may use heat conduction from a probe heated to a glowing temperature by a direct current (much in the manner of a soldering iron). This may be accomplished by direct current from dry-cells in a penlight-type device. Electrocauterization may be include the process of destroying tissue (or cutting through soft tissue) using heat conduction from a metal probe heated by electric current. The procedure stops bleeding from small vessels (larger vessels being ligated). Electrocautery may apply high frequency alternating current by a unipolar or bipolar method. It can be a continuous waveform to cut tissue, or intermittent to coagulate tissue. Electrocautery may use electrical current to heat a metal wire that is then applied to the target tissue in order to burn or coagulate the specific area of tissue. It is not used to pass the current through tissue, but rather is applied directly onto the targeted area of treatment. Using this technique, heat is passed through a resistant metal wire which is used as an electrode. This hot electrode may then be placed directly onto the treatment area destroying that specific tissue.

SUMMARY OF EXEMPLARY EMBODIMENTS OF THE INVENTION

An aspect of an embodiment provides a laparoscopic or thoracoscopic port that allows cauterization along a site of s subject. An aspect of an embodiment provides a sheath (such as an expandable sheath) to be implemented with a laparoscopic or thoracoscopic port that allows cauterization along the body walls of a site of s subject. An aspect of an embodiment provides a port that cauterizes, which may be implemented for any type of laparoscopic, thoracoscopic, or endoscopic surgery or procedure. An aspect of an embodiment provides a sheath to be implemented with a port, whereby the sheath is configured to cauterize and may be implemented for any type of laparoscopic, thoracoscopic, or endoscopic surgery or procedure.

The present inventors submit that various surgical operations are performed minimally invasively through small circular plastic or metal ports enabling instruments to reach organs from outside the skin. The present inventors note that problems and complications that are associated with the current aforementioned operations (e.g., endoscopic) whereby when ports are removed, small vessels in the chest or abdominal wall (or other region) can bleed which can be difficult to fix. An aspect of an embodiment of the present invention provides a port device and/or expandable sheath device and related methods of use that allows for electrocautery to be performed by attaching a conducting surface on its tip (or other required or desired location of the device) that is disposed inside the chest or abdominal wall (or other region or target of the subject/patient) that would allow directed cautery of any site that is bleeding. The port device or sheath can be used upon entry as well to minimize bleeding from chest or abdominal wall (or other applicable region) during access. The port device may be in communication with a camera (or other recording device) that allows visualization from inside the shaft of the port to view the site as electrocautery is implemented to ensure any bleeding is ceased.

An aspect of an embodiment provides a port that cauterizes for use in laparoscopic, endoscopic or thoracic surgery.

An aspect of an embodiment of the present invention provides, but not limited thereto, a port apparatus for use for providing electrocautery for surgery on a site of a subject. The apparatus may comprise: a trocar device, wherein the trocar device having a distal portion and a proximal portion separated longitudinally from one another; a diode disposed on the distal portion of the trocar device; an electro-surgical terminal disposed on the proximal portion of the trocar device; and a wire disposed longitudinally on the trocar device, wherein the wire is in communication with the diode and the electro-surgical terminal.

An aspect of an embodiment of the present invention provides, but not limited thereto, a device for use with a port apparatus for use for providing electrocautery for surgery on a site of a subject. The device may comprise: an expandable sheath device, wherein the expandable sheath device having a distal portion and a proximal portion separated longitudinally from one another; a diode disposed on the distal portion of the expandable sheath device; an electro-surgical terminal disposed on the proximal portion of the expandable sheath device; and a wire disposed longitudinally on the expandable sheath device, wherein the wire is in communication with the diode and the electro-surgical terminal.

An aspect of an embodiment of the present invention provides, but not limited thereto, a method for performing electrocautery on a site of a subject. The method may comprise: inserting a trocar device into the location of the site of the subject, wherein the trocar device having a distal portion and a proximal portion separated longitudinally from one another; and electro-cauterizing the site of the subject using a diode disposed on the trocar device.

An aspect of an embodiment of the present invention provides, but not limited thereto, a method for performing electrocautery on a site of a subject. The method may comprise: inserting one or more medical tubes or medical instruments or devices that extends longitudinally through an expandable sheath; wherein the expandable sheath having a distal portion and a proximal portion separated longitudinally from one another; and electro-cauterizing the site of the subject using a diode disposed on the expandable sheath device.

An aspect of an embodiment of the present invention provides, but not limited thereto, a port apparatus (or other type of medical apparatus or device) for use for providing electrocautery for surgery on a site of a subject. The port apparatus (or the other type of medical apparatus or device) may comprise: a medical tube or medical instrument or device, wherein the medical tube or medical instrument or device having a distal portion and a proximal portion separated longitudinally from one another; a diode disposed on the distal portion of the medical tube or medical instrument or device; an electro-surgical terminal disposed on the proximal portion of the medical tube or medical instrument or device; and a wire disposed longitudinally on the medical tube or medical instrument or device, wherein the wire is in communication with the diode and the electro-surgical terminal.

An aspect of an embodiment of the present invention provides, but not limited thereto, a method and apparatus for performing electrocautery on a site of a subject that includes inserting a trocar device into the location of the site of the subject and electro-cauterizing the site of the subject using a diode included with the trocar device. An aspect of an embodiment of the present invention provides, but not limited thereto, a method and apparatus for performing electrocautery on a site of a subject that includes inserting one or more medical tubes or medical instruments or devices that extends through an expandable sheath; and electro-cauterizing the site of the subject using a diode included with the expandable sheath device.

It should be appreciated that any of the components or modules referred to with regards to any of the present invention embodiments discussed herein, may be integrally or separately formed with one another. Further, redundant functions or structures of the components or modules may be implemented. Moreover, the various components may be communicated locally and/or remotely with any user/clinician/patient or machine/system/computer/processor. Moreover, the various components may be in communication via wireless and/or hardwire or other desirable and available communication means, systems and hardware. Moreover, various components and modules may be substituted with other modules or components that provide similar functions.

It should be appreciated that the device and related components discussed herein may take on all shapes along the entire continual geometric spectrum of manipulation of x, y and z planes to provide and meet the anatomical, environmental, and structural demands and operational requirements. Moreover, locations and alignments of the various components may vary as desired or required.

It should be appreciated that various sizes, dimensions, contours, rigidity, shapes, flexibility and materials of any of the components or portions of components in the various embodiments discussed throughout may be varied and utilized as desired or required.

It should be appreciated that while some dimensions are provided on the aforementioned figures, the device may constitute various sizes, dimensions, contours, rigidity, shapes, flexibility and materials as it pertains to the components or portions of components of the device, and therefore may be varied and utilized as desired or required.

Although example embodiments of the present disclosure are explained in detail herein, it is to be understood that other embodiments are contemplated. Accordingly, it is not intended that the present disclosure be limited in its scope to the details of construction and arrangement of components set forth in the following description or illustrated in the drawings. The present disclosure is capable of other embodiments and of being practiced or carried out in various ways.

It must also be noted that, as used in the specification and the appended claims, the singular forms "a," "an" and "the" include plural referents unless the context clearly dictates otherwise. Ranges may be expressed herein as from "about" or "approximately" one particular value and/or to "about" or "approximately" another particular value. When such a range is expressed, other exemplary embodiments include from the one particular value and/or to the other particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the present disclosure. Similarly, it is also to be understood that the mention of one or more components in a device or system does not preclude the presence of additional components or intervening components between those components expressly identified.

As discussed herein, a "subject" may be any applicable human, animal, or other organism, living or dead, or other biological or molecular structure or chemical environment, and may relate to particular components of the subject, for instance specific tissues or fluids of a subject (e.g., human tissue in a particular area of the body of a living subject), which may be in a particular location of the subject, referred to herein as an "area of interest" or a "region of interest."

Some references, which may include various patents, patent applications, and publications, are cited in a reference list and discussed in the disclosure provided herein. The citation and/or discussion of such references is provided merely to clarify the description of the present disclosure and is not an admission that any such reference is "prior art"

to any aspects of the present disclosure described herein. In terms of notation, "[n]" corresponds to the nth reference in the list. All references cited and discussed in this specification are incorporated herein by reference in their entireties and to the same extent as if each reference was individually incorporated by reference.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 10% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, 4.24, and 5). Similarly, numerical ranges recited herein by endpoints include subranges subsumed within that range (e.g. 1 to 5 includes 1-1.5, 1.5-2, 2-2.75, 2.75-3, 3-3.90, 3.90-4, 4-4.24, 4.24-5, 2-5, 3-5, 1-4, and 2-4). It is also to be understood that all numbers and fractions thereof are presumed to be modified by the term "about."

The invention itself, together with further objects and attendant advantages, will best be understood by reference to the following detailed description, taken in conjunction with the accompanying drawings.

BRIEF DESCRIPTION OF THE DRAWINGS

The foregoing and other objects, features and advantages of the present invention, as well as the invention itself, will be more fully understood from the following description of preferred embodiments, when read together with the accompanying drawings.

The accompanying drawings, which are incorporated into and form a part of the instant specification, illustrate several aspects and embodiments of the present invention and, together with the description herein, serve to explain the principles of the invention. The drawings are provided only for the purpose of illustrating select embodiments of the invention and are not to be construed as limiting the invention.

DETAILED DESCRIPTION OF EXEMPLARY EMBODIMENTS

Figure 1:
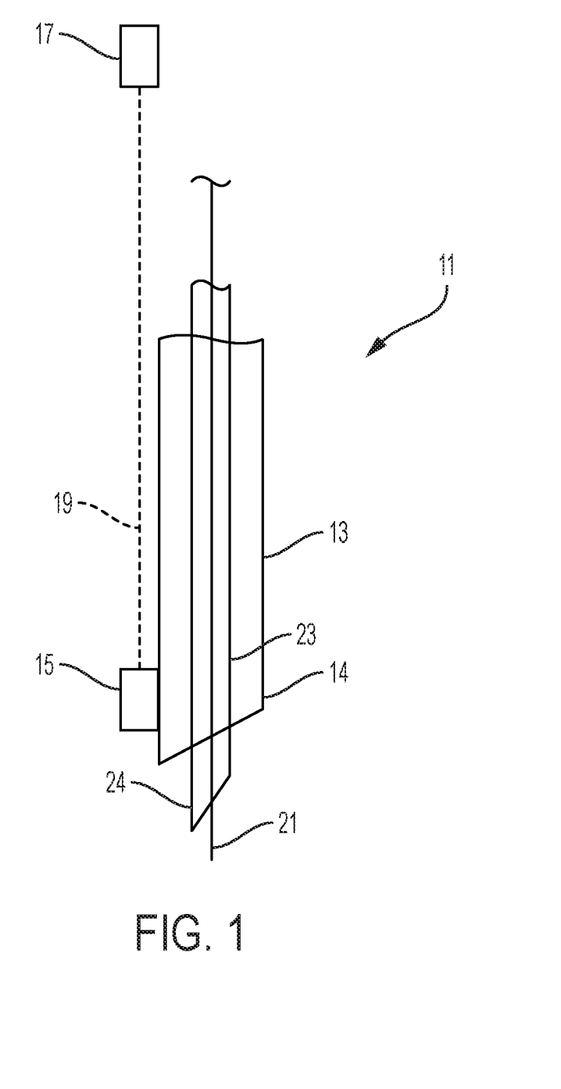
FIG. 1 schematically illustrates a port apparatus for electrocautery for surgery.

FIG. 1 schematically illustrates an embodiment of a port apparatus 11 that is configured for use for providing electrocautery for surgery on a site of a subject. The port apparatus 11 may include a trocar device 13, whereby the trocar device 13 may have a distal portion 14 and a proximal portion 12 (not shown) separated longitudinally from one another. Also shown is a needle 21 that may be inserted or extended longitudinally through the trocar device 13. Also included is a diode 15 disposed on the distal portion 14 of the trocar device 13. The diode 15 may be any electrode, contact, or device configured for delivering the electrocautery effect to the applicable site. Further, an electro-surgical terminal 17 may disposed on the proximal portion 12 (not shown) of the trocar device 13. Moreover, a wire 19 may disposed longitudinally on the trocar device 13, wherein the wire 19 is in communication with the diode 15 and the electro-surgical terminal 17. For example, the wire 19 may be embedded within the wall or integral with the wall of the trocar device 13 so as to avoid allowing the wire to make direct electrical contact with the subject. The wire 19 may be any transmission medium, conductive path, line, channel or circuit for transmitting the applicable the electric current to ultimately cause the thermal conduction or heat to provide the cauterization. The wire or other components may be covered with a coating for electric insulation.

An aspect of an embodiment of present invention provides, among other things, a method for performing electrocautery on a site of a subject. The method may include inserting the trocar device 13 (or other medical instrument or devices) into the location of the site of the subject. The method further includes electro-cauterizing the site of the subject using a diode (or other electrode or hardware) disposed on the trocar device.

Figure 2:
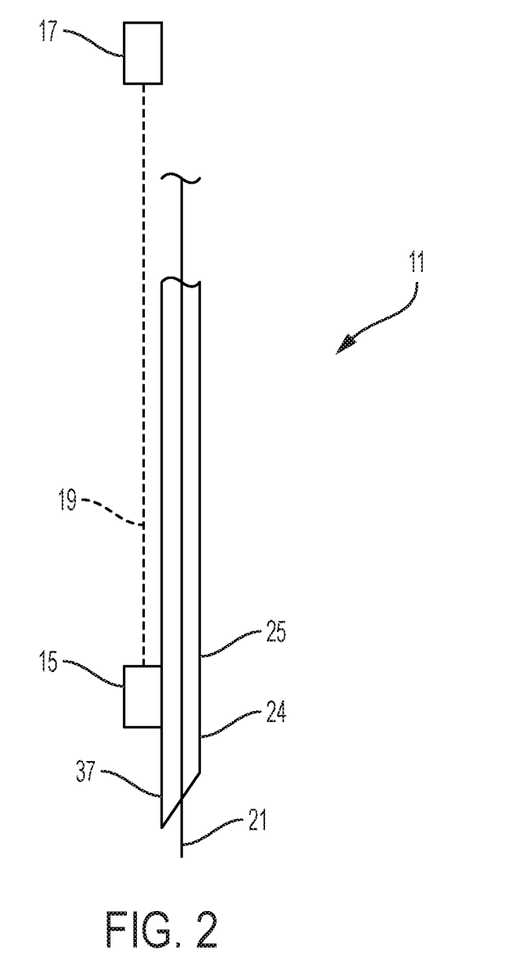
FIG. 2 schematically illustrates sheath in a non-expanded state for use with a port apparatus for electrocautery for surgery.
Figure 3:
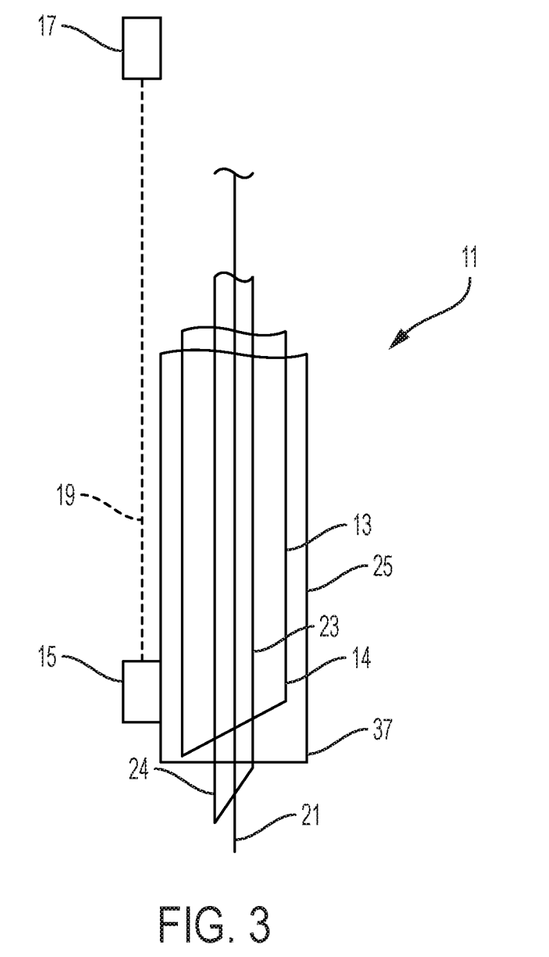
FIG. 3 schematically illustrates sheath in an expanded state for use with a port apparatus for electrocautery for surgery.

FIGS. 2-3 schematically illustrates an embodiment of a sheath in a non-expanded state and an expanded state, respectively, for use with a port apparatus 11 for electrocautery for surgery. The port apparatus 11 may include a trocar device 13, whereby the trocar device 13 may have a distal portion 14 and a proximal portion 12 (not shown) separated longitudinally from one another. Additionally, an expandable sheath 25 may be included, whereby the expandable sheath 25 may have a distal portion 37 and a proximal portion 36 (not shown) separated longitudinally from one another. Also shown is a needle 21 that may be inserted or extended longitudinally through the trocar device 13 and/or expandable sheath 25. Also included is a diode 15 disposed on the distal portion 37 of the expandable sheath 25. The diode 15 may be any electrode, contact, or device configured for delivering the electrocautery effect to the applicable site. Further, an electro-surgical terminal 17 may disposed on the proximal portion 36 (not shown) of the expandable sheath 25. Moreover, a wire 19 may disposed longitudinally on the expandable sheath 25, wherein the wire 19 is in communication with the diode 15 and the electro-surgical terminal 17. For example, the wire 19 may be embedded within the wall or integral with the wall of the expandable sheath 25 so as to avoid allowing the wire to make direct electrical contact with the subject. The wire 19 may be any transmission medium, conductive path, line, channel or circuit for transmitting the applicable electrical current so at to ultimately provide the thermal conduction or heat conduction for the cauterization. In an embodiment, the wire or other components may be covered with a coating for electric insulation.

An aspect of an embodiment of present invention provides, among other things, a method for performing electrocautery on a site of a subject. The method may include inserting one or more tubes (e.g., cannulas) or medical instruments or devices that extends longitudinally through an expandable sheath The method further includes electrocauterizing the site of the subject using a diode disposed on the expandable sheath device. The sheath expands radially due to the radial forces applied outward onto the sheath while the tube (e.g., cannula) or other medical instruments or devices are inserted, extended, or disposed within the expandable sheath. In an embodiment a sheath may be utilized that is not configured to be expandable. In an embodiment a sheath may utilized that is of a self-deployed configuration.

Figure 4:
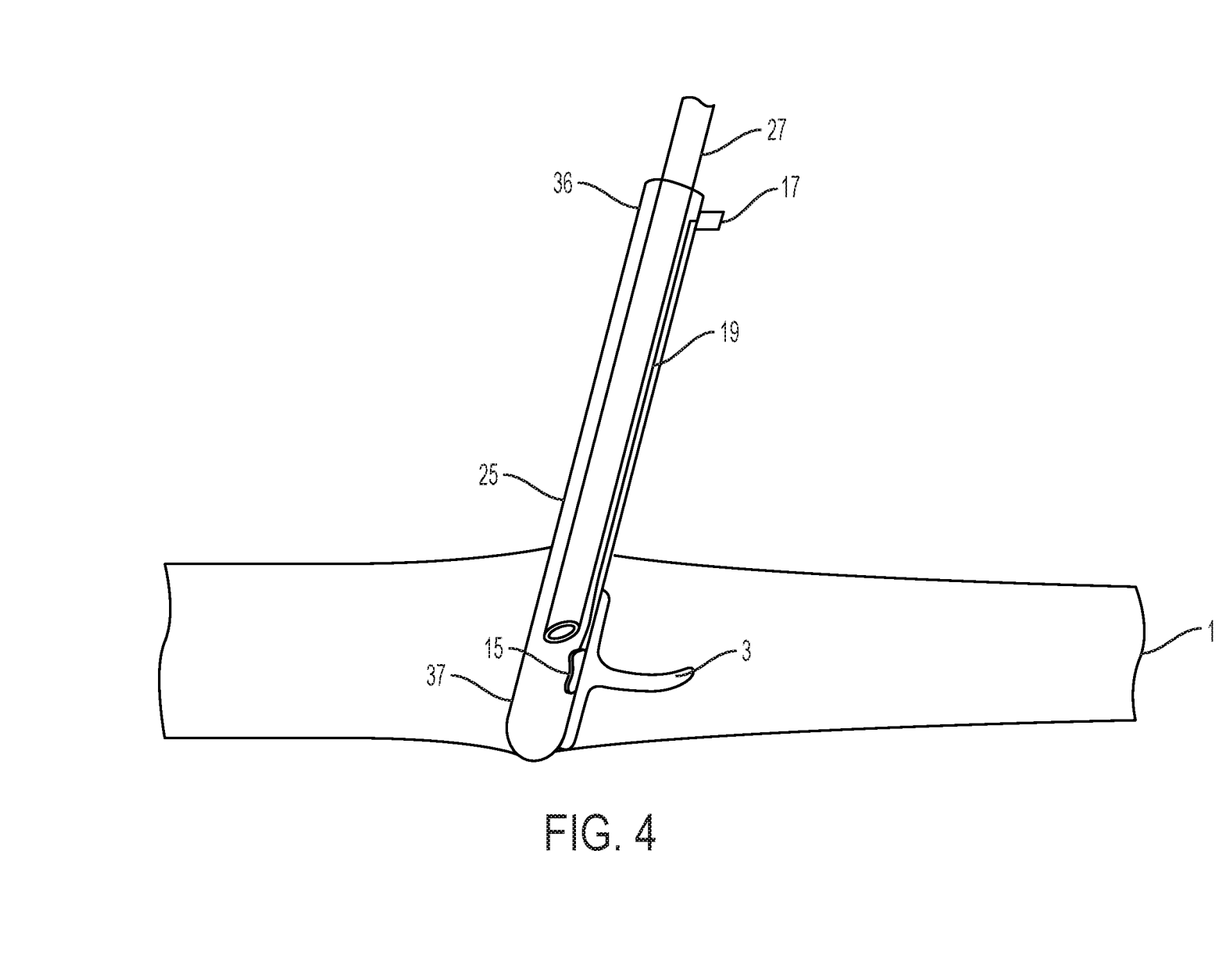
FIG. 4 schematically illustrates a sheath, along with an endoscope, for use with a port apparatus for electrocautery for surgery.
Figure 5:
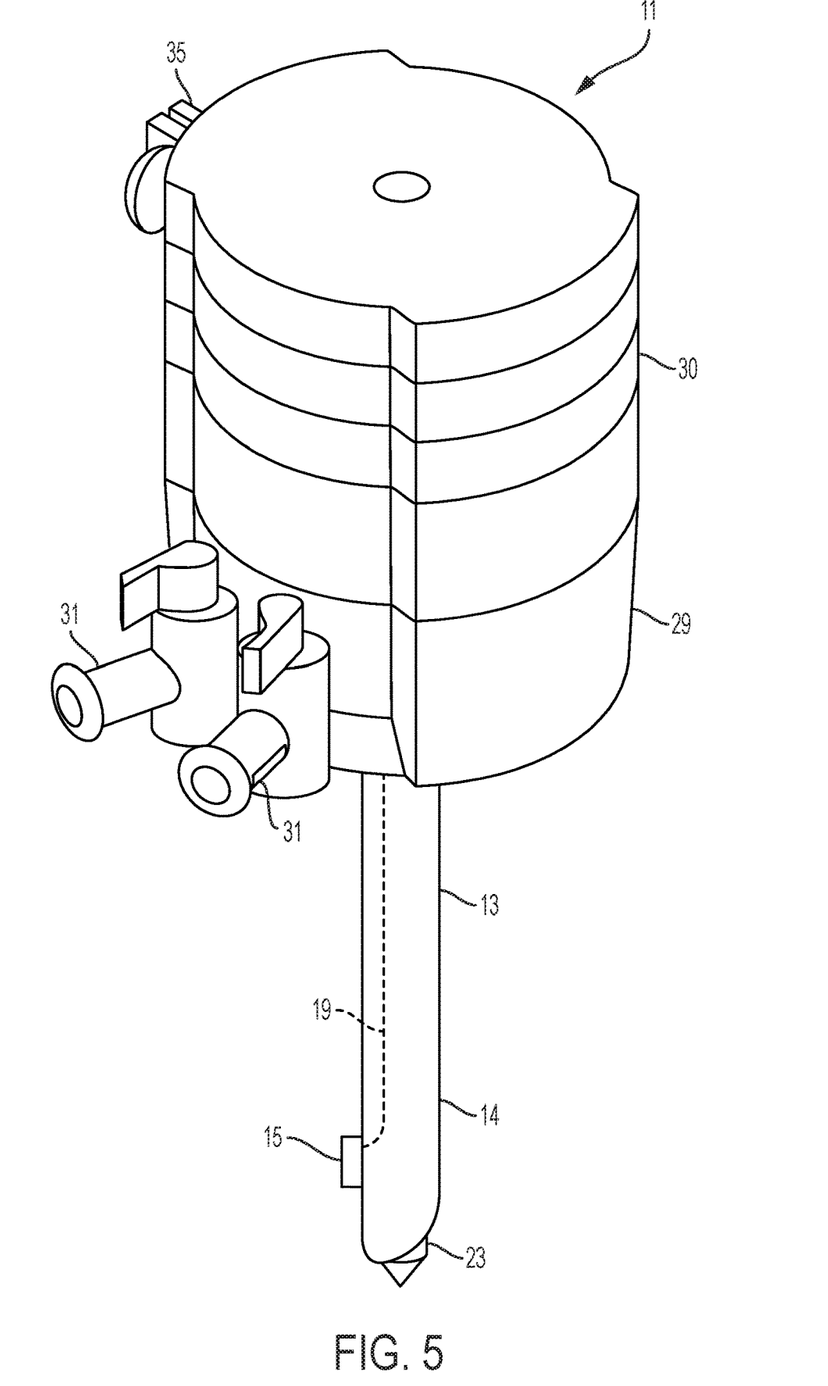
FIG. 5 schematically illustrates a port apparatus, including a trocar and dilator, for electrocautery for surgery.
Figure 6:
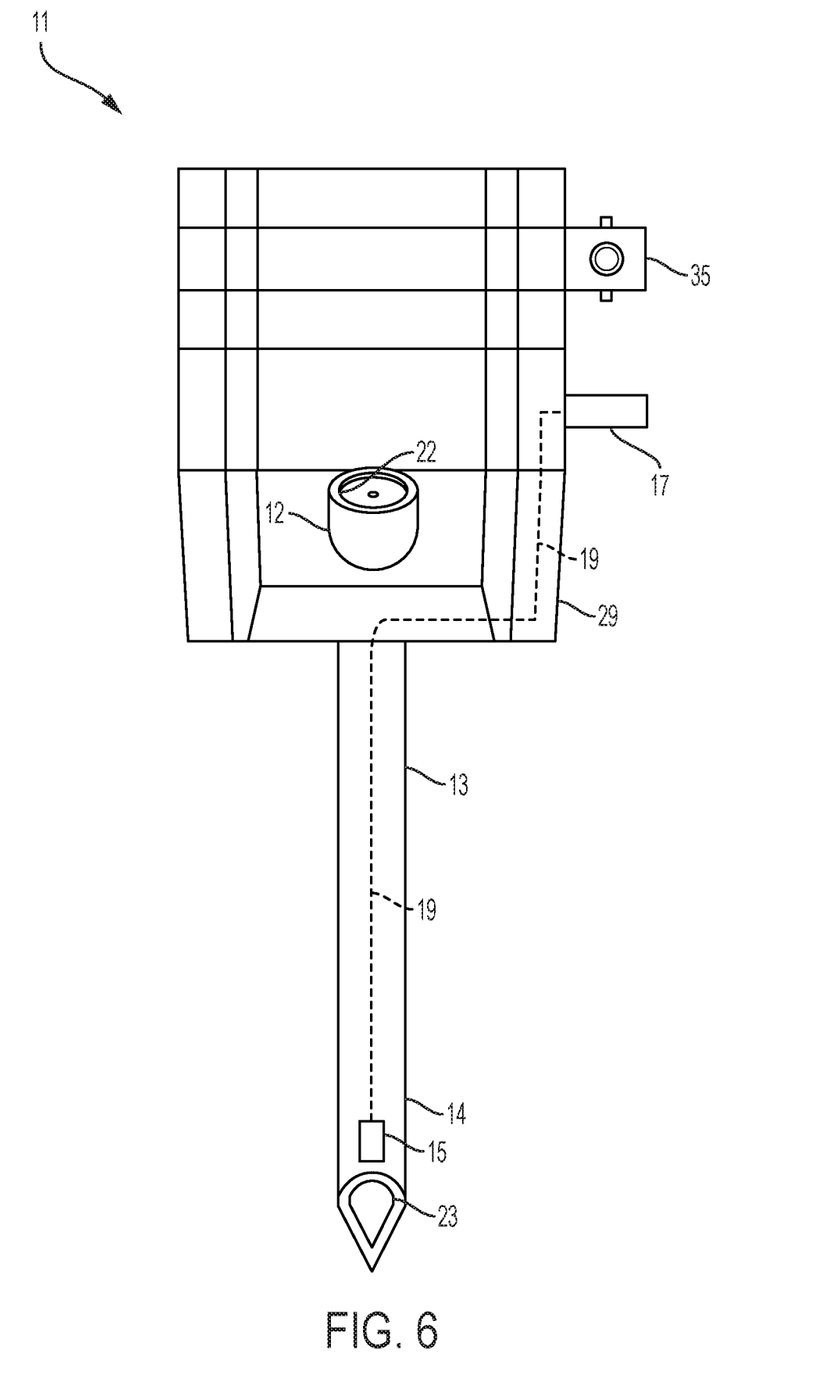
FIG. 6 schematically illustrates a port apparatus, including a trocar and dilator, for electrocautery for surgery.
Figure 7:
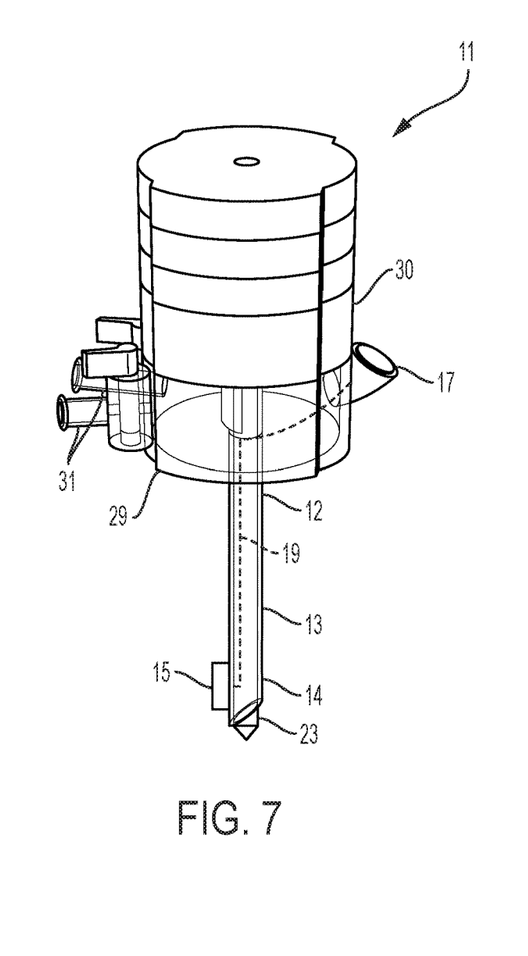
FIG. 7 schematically illustrates a port apparatus, including a trocar and dilator, for electrocautery for surgery.
Figure 8:
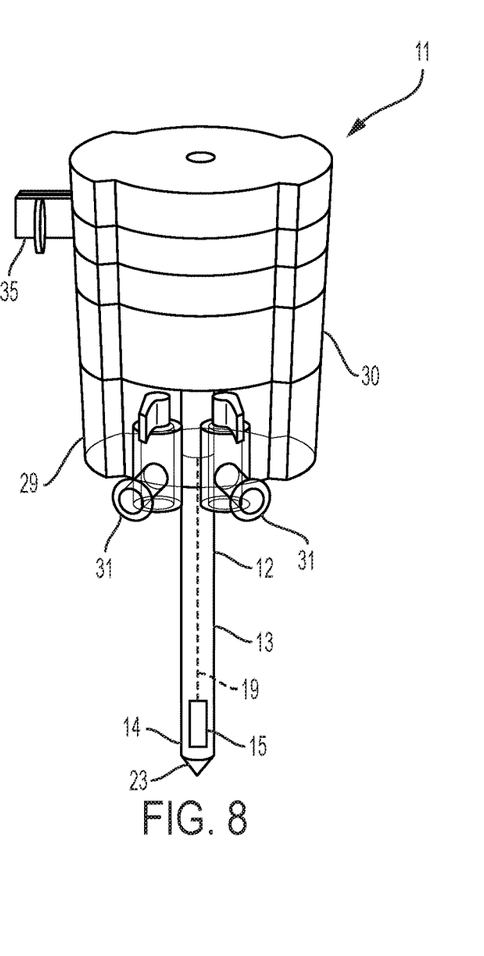
FIG. 8 schematically illustrates a port apparatus, including a trocar and dilator, for electrocautery for surgery.
Figure 9:
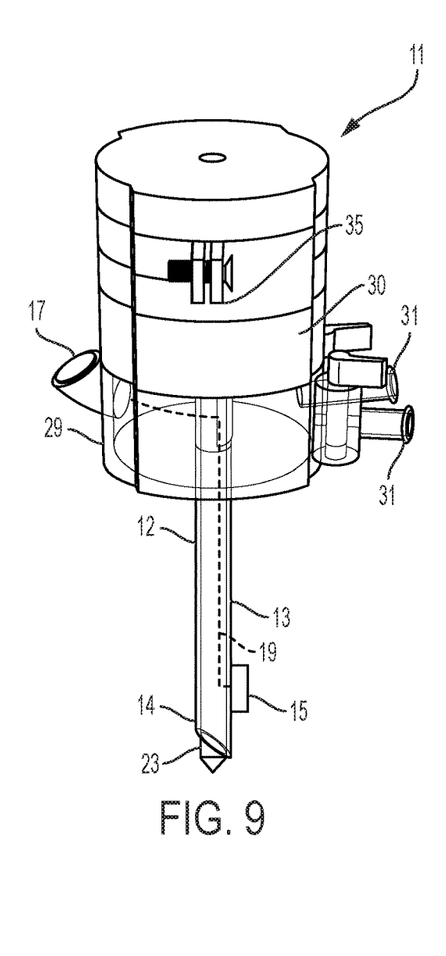
FIG. 9 schematically illustrates a port apparatus, including a trocar and dilator, for electrocautery for surgery.

FIG. 4 schematically illustrates an embodiment of an expandable sheath 25 that may be used with a port apparatus (not shown), for example, for electrocautery for surgery of a site 3 in the tissue wall 1 or other region of the subject. The expandable sheath 25 may have a distal portion 37 and a proximal portion 36 separated longitudinally from one another. Also shown is an endoscope 27 (of which may be other medical instruments or medical devices) that may be inserted or extended longitudinally through expandable sheath 25. Also included is a diode 15 disposed on the distal portion 37 of the expandable sheath 25. The diode 15 may be any electrode, contact, or device configured for providing the electrocautery effect to the applicable site. Further, an electro-surgical terminal 17 may be disposed on the proximal portion 36 of the expandable sheath 25. Moreover, a wire 19 may disposed longitudinally on the expandable sheath 25, wherein the wire 19 is in communication with the diode 15 and the electro-surgical terminal 17. For example, the wire 19 may be embedded within the wall or integral with the wall of the expandable sheath 25 so as to avoid allowing the wire to make direct electrical contact with the subject. The wire 19 may be any transmission medium, conductive path, line, channel or circuit for transmitting the applicable electrical current so at to ultimately provide the thermal conduction or heat conduction. In an embodiment, the wire or other components may coated to provide electric insulation. The electro-surgical terminal 17 may be locate at a variety of locations of the apparatus or device as desired or required.

FIGS. 5, 6, 7, 8, 9, 10, 11, and 12 schematically illustrate different views of various embodiments of a port apparatus 11 that is configured for use for providing electrocautery for surgery on a site of a subject. The port apparatus 11 may include a trocar device 13, whereby the trocar device 13 may have a distal portion 14 and a proximal portion 12 separated longitudinally from one another. Although not shown, various instruments and devices may be inserted or extended longitudinally through the trocar device 13 or other related components used as part of or with the port apparatus. Also included is a diode 15 disposed on the distal portion 14 of the trocar device 13 (shown in FIGS. 5, 6, 7, 8 and 9). The diode 15 may be any electrode, contact, component, or device configured for delivering the electrocautery effect to the applicable site. Further, an electro-surgical terminal 17 may disposed on or near the trocar interface portion 29 (shown in FIGS. 6, 7 and 9). Moreover, a wire 19 may disposed longitudinally on the trocar device 13, wherein the wire 19 is in communication with the diode 15 and the electro-surgical terminal 17. For example, the wire 19 may be embedded within the wall or integral with the wall of the trocar device 13 so as to avoid allowing the wire to make direct electrical contact with the subject. The wire 19 may be any transmission medium, line, conductive path, channel or circuit for transmitting the applicable electric current to ultimately cause the thermal conduction or heat for the electric cautery. Also shown in some of FIGS. 5-12, provided are the dilator interface portions 30, orifices 31, and 36 camera support 35. The dilator interface portions 30 may be located at or near the proximal end of the dilator 23 and accessible for the practitioner, surgeon, clinician, or user; as well as receptive to other instruments or devices. The orifices 31 are configured for an output, input, or both an output and input between the subject and outside of the subject to exchange smoke, air, fluid, or gas (or other medium as needed or required). The orifices 31 may be operable as or with luer lock fittings, for example, but not limited thereto. The port apparatus 11 may be used with an image recording device (such as a camera, video recording or other imaging means) as well as other devices and surgical and medical instruments to be disposed or mounted on the camera support 35, for example. The camera (or recording device) may be secured a variety of ways such as at the camera support 35 or within the trocar, or other suitable location (s), for example. The acquired image or related data may be communicated locally and/or remotely to the surgeon, clinician, user, and/or processor. Similarly, any data or information acquired by the components, equipment, or instruments associated with the port apparatus may be communicated locally and/or remotely to the surgeon, clinician, user, and/or processor.

Figure 10:
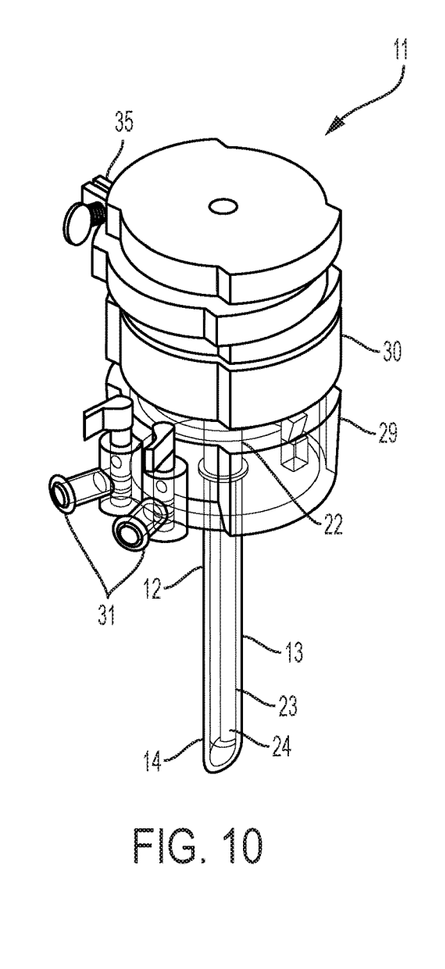
FIG. 10 schematically illustrates a partially exploded view of a port apparatus, including a trocar and dilator, for electrocautery for surgery.
Figure 11:
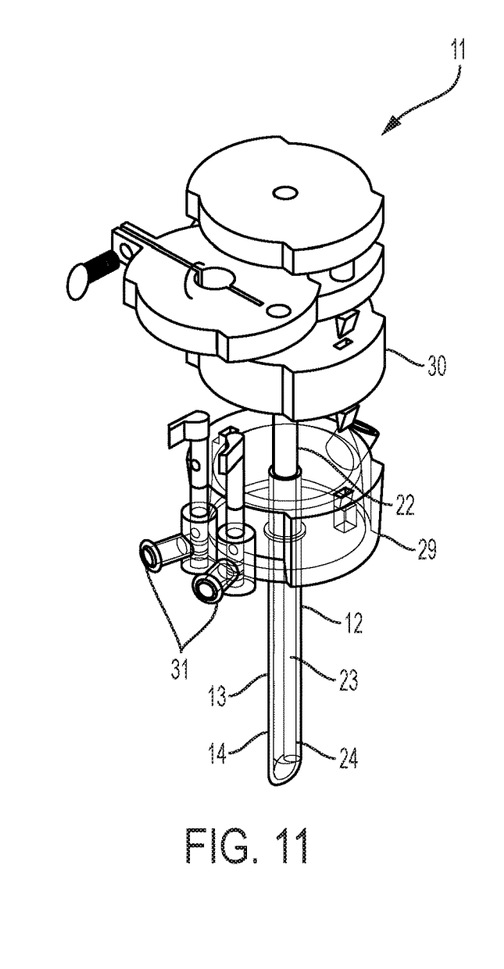
FIG. 11 schematically illustrates a partially exploded view of a port apparatus, including a trocar and dilator, for electrocautery for surgery.
Figure 12:
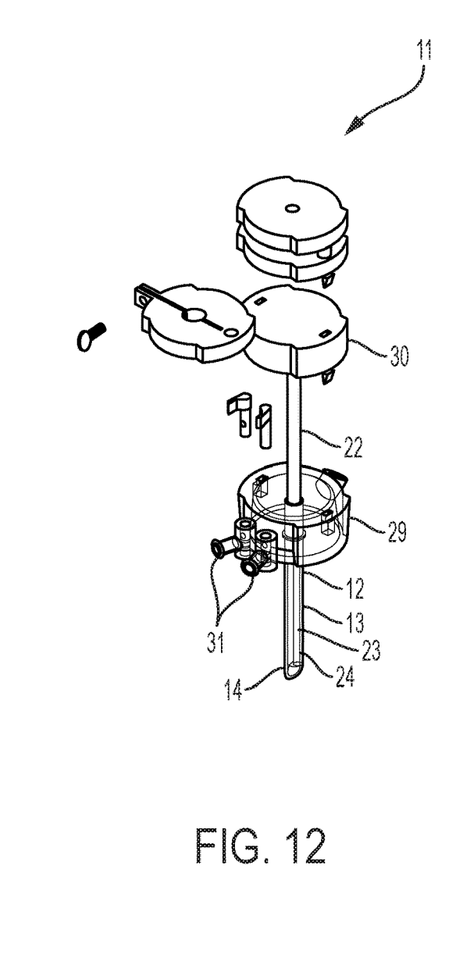
FIG. 12 schematically illustrates an exploded view of a port apparatus, including a trocar and dilator, for electrocautery for surgery.

FIGS. 10, 11, and 12 schematically illustrates varying exploded views of a port apparatus, including a trocar and dilator, for electrocautery for surgery.

Figure 13:
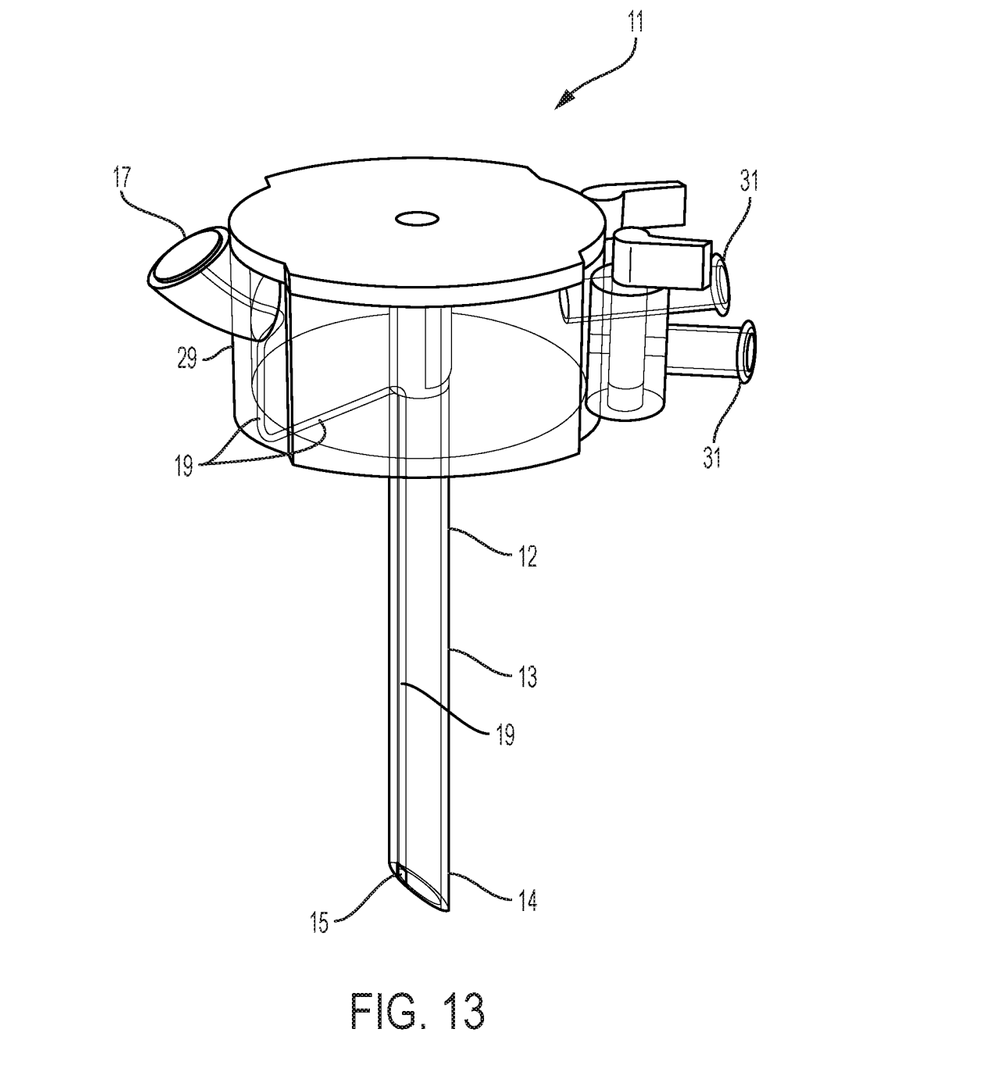
FIG. 13 schematically illustrates a port apparatus including a trocar for electrocautery for surgery.

FIG. 13 schematically illustrates an embodiment of a port apparatus 11 that is configured for use for providing electrocautery for surgery on a site of a subject. The port apparatus 11 may include a trocar device 13, whereby the trocar device 13 may have a distal portion 14 and a proximal portion 12 separated longitudinally from one another. Although not shown, various instruments and devices may be inserted or extended longitudinally through the trocar device 13 or other related components used as part of or with the port apparatus. Also included is a diode 15 disposed on the distal portion 14 of the trocar device 13. The diode 15 may be any electrode, contact, component, or device configured for delivering the electrocautery effect to the applicable site. Further, an electro-surgical terminal 17 may disposed on the trocar interface portion 29. Moreover, a wire 19 may disposed longitudinally on the trocar device 13, wherein the wire 19 is in communication with the diode 15 and the electro-surgical terminal 17. For example, the wire 19 may be embedded within the wall or integral with the wall of the trocar device 13 so as to avoid allowing the wire to make direct electrical contact with the subject. For example, the wire 19 may be situated with, connected to, or in communication with the wall of the trocar device 13 and have a covering so as to avoid allowing the wire to make direct electrical contact with the subject. The wire 19 may be any transmission medium, conductive path, line, channel or circuit for transmitting the applicable the electric current to ultimately cause the thermal conduction or heat for the cauterization. Also shown are the orifices 31 and camera support 35.

The various components other than the specific electric cautery components may be a variety of materials such as, but not limited thereto, plastic, stainless steel, polycarbonate, nylon, polymers, acetal polymers, ceramics, etc.

In an embodiment, the electro-surgical terminal 17 may be any connection, terminal, or point to provide or facilitate a connection with electro-surgical power or other applicable power or energy supply. In an embodiment, the electro-surgical terminal may 17 be configured to facilitate quick-release connection to and disconnection from an electrosurgical power supply or other applicable power supply.

In an embodiment, the electrical/electronic related components/system including the diode, wire, and electro-surgical terminal may be any suitable electrically conductive material such that current supplied by power supply is delivered through the cauterizing diode tip or distal portion (or other applicable portion) of the trocar, sheath, or other medical instrument or device so as to target site in the subject.

EXAMPLES

Practice of an aspect of an embodiment (or embodiments) of the invention will be still more fully understood from the following examples and experimental results, which are presented herein for illustration only and should not be construed as limiting the invention in any way.

Example 1. A port apparatus for use for providing electrocautery for surgery on a site of a subject. The apparatus may comprise: a trocar device, wherein said trocar device having a distal portion and a proximal portion separated longitudinally from one another; a diode disposed on said distal portion of said trocar device; an electro-surgical terminal disposed on said proximal portion of said trocar device; and a wire disposed longitudinally on said trocar device, wherein said wire is in communication with said diode and said electro-surgical terminal.

Example 2. The port apparatus of example 1, wherein: said trocar device is configured to receive a needle that extends longitudinally through said trocar device.

Example 3. The port apparatus of example 2, wherein: said trocar device is configured to receive a dilator that extends longitudinally through said trocar device.

Example 4. The port apparatus of example 1 (as well as subject matter of one or more of any combination of examples 2-3, in whole or in part), wherein: said trocar device is configured to receive a dilator that extends longitudinally through said trocar device.

Example 5. The port apparatus of example 1 (as well as subject matter of one or more of any combination of examples 2-4, in whole or in part), wherein said apparatus is used as a laparoscopic or thoracoscopic port for laparoscopic or thoracoscopic surgery, respectively.

Example 6. A device for use with a port apparatus for use for providing electrocautery for surgery on a site of a subject. The device may comprise: an expandable sheath device, wherein said expandable sheath device having a distal portion and a proximal portion separated longitudinally from one another; a diode disposed on said distal portion of said expandable sheath device; an electro-surgical terminal disposed on said proximal portion of said expandable sheath device; and a wire disposed longitudinally on said expandable sheath device, wherein said wire is in communication with said diode and said electro-surgical terminal.

Example 7. The device of example 6, wherein: said expandable sheath device is configured to receive one or more medical tubes or one or more medical instruments or devices that extend longitudinally through said expandable sheath.

Example 8. The device of example 7, wherein said expandable sheath is configured to expand radially outward into an expanded state upon receiving said one or more medical tubes or one or more medical instruments or devices that have a radius larger than the radius of said expandable sheath in an unexpanded state.

Example 9. The device of example 7 (as well as subject matter in whole or in part of example 8), wherein said one or more medical tubes include any combination of one or more of the following: cannula, trocar device, needle, dilator, laparoscope, thoracoscope, or endoscope.

Example 10. The port apparatus of example 6 (as well as subject matter of one or more of any combination of examples 5-9, in whole or in part), wherein said apparatus is used as a laparoscopic or thoracoscopic port for laparoscopic or thoracoscopic surgery, respectively.

Example 11. A method for performing electrocautery on a site of a subject. The method may comprise: inserting a trocar device into the location of the site of the subject, wherein said trocar device having a distal portion and a proximal portion separated longitudinally from one another; and electro-cauterizing the site of the subject using a diode disposed on said trocar device.

Example 12. The method of example 11, comprises: inserting a needle that extends longitudinally through said trocar device.

Example 13. The method of example 12, comprises: inserting a dilator that extends longitudinally through said trocar device.

Example 14. The method of example 11 (as well as subject matter in whole or in part of example 13), comprises: inserting a dilator that extends longitudinally through said trocar device.

Example 15. The method of example 11 (as well as subject matter of one or more of any combination of examples 12-14, in whole or in part), wherein said method is used for laparoscopic or thoracoscopic surgery, respectively.

Example 16. A method for performing electrocautery on a site of a subject. The method may comprise: inserting one or more medical tubes or medical instruments or devices that extends longitudinally through an expandable sheath; wherein said expandable sheath having a distal portion and a proximal portion separated longitudinally from one another; and electro-cauterizing the site of the subject using a diode disposed on said expandable sheath device.

Example 17. The method of example 16, comprises expanding said expandable sheath to expand radially outward into an expanded state upon receiving said one or more inserted medical tubes or medical instruments or devices that have a radius larger than the radius of said expandable sheath in an unexpanded state.

Example 18. The method of example 17, wherein said one or more medical tubes include any combination of one or more of the following: cannula, trocar device, needle, dilator, laparoscope, thoracoscope, or endoscope.

Example 19. The method of example 16 (as well as subject matter in whole or in part of example 18), wherein said method is used for laparoscopic or thoracoscopic surgery, respectively.

Example 20. A port apparatus for use for providing electrocautery for surgery on a site of a subject. The apparatus may comprise: a medical tube or medical instrument or device, wherein said medical tube or medical instrument or device having a distal portion and a proximal portion separated longitudinally from one another; a diode disposed on said distal portion of said medical tube or medical instrument or device; an electro-surgical terminal disposed on said proximal portion of said medical tube or medical instrument or device; and a wire disposed longitudinally on said medical tube or medical instrument or device, wherein said wire is in communication with said diode and said electro-surgical terminal.

Example 21. The apparatus of example 20 (as well as subject matter of one or more of any combination of examples 2-5 and 7-10, in whole or in part), wherein said medical tube or medical instrument or device includes any combination of one or more of the following: cannula, trocar device, needle, dilator, laparoscope, thoracoscope, or endoscope.

Example 22. The method of using any of the devices, systems, apparatuses, assemblies, or their components provided in any one or more of examples 1-21.

Example 23. The method of providing instructions to use or operate of any of the devices, systems, apparatuses, assemblies, or their components provided in any one or more of examples 1-24.

Example 25. The method of manufacturing any of the devices, systems, apparatuses, assemblies, or their components provided in any one or more of examples 1-21.

Example 26. A method and an apparatus (as well as subject matter of one or more of any combination of examples 1-21, in whole or in part) for performing electrocautery on a site of a subject that includes inserting a trocar device into the location of the site of the subject and electro-cauterizing the site of the subject using a diode included with the trocar device.

Example 27. A method and an apparatus (as well as subject matter of one or more of any combination of examples 1-21, in whole or in part) for performing electrocautery on a site of a subject that includes inserting one or more medical tubes or medical instruments or devices that extends through an expandable sheath; and electro-cauterizing the site of the subject using a diode included with the expandable sheath device.

Example 28. It is noted that machine readable medium or computer useable medium may be configured to execute the subject matter pertaining to system (or apparatus) or related methods disclosed in examples 1-21, as well as examples 22-27.

REFERENCES

The devices, systems, apparatuses, compositions, machine readable medium, computer program products, and methods of various embodiments of the invention disclosed herein may utilize aspects disclosed in the following references, applications, publications and patents and which are hereby incorporated by reference herein in their entirety, and which are not admitted to be prior art with respect to the present invention by inclusion in this section:

1. U.S. Pat. No. 5,776,126, Wilk, et al., "Laparoscopic Surgical Apparatus and Associated Method", Jul. 7, 1998.

2. U.S. Pat. No. 5,830,214, Flom, et al., "Fluid-evacuating Electrosurgical Device", Nov. 3, 1998.

3. U.S. Pat. No. 7,604,648 B2, Kerr, S., "Direct Vision Port Site Dissector", Oct. 20, 2009.

4. U.S. Patent Application Publication No. US 2008/0242939 A1, Johnston, W., "Retractor System for Internal In-Situ Assembly during Laparoscopic Surgery", Oct. 2, 2008.

5. U.S. Pat. No. 8,764,765 B2, Piskun, G., et al., "Laparoscopic Instrument and Related Surgical Method", Jul. 1, 2014.

6. European Patent Application No. EP 2316360 A1, Farascioni, D., "Radially Expandable Access System Including Trocar Seal", May 4, 2011.

7. U.S. Pat. No. 5,387,197, Smith, R., et al., "Trocar Safety Shield Locking Mechanism", Feb. 7, 1995.

8. U.S. Pat. No. 6,187,002 B1, Long, G., et al., "Capacitive Electrosurgical Trocar Including Adapter", Feb. 13, 2001.

9. U.S. Pat. No. 9,125,573 B2, Koyrakh, L., et al., "Electrically Transparent Introducer Sheath", Sep. 8, 2015.

10. U.S. Pat. No. 5,925,041, Long, G., et al., "Monopolar Electrosurgical Trocar", Jul. 20, 1999.

11. U.S. Pat. No. 5,658,279, Nardella, P., et al., "Bipolar Electrosurgical Trocar", Aug. 19, 1997.

12. U.S. Pat. No. 6,451,017 B1, Moutafis, T., et al., "Surgical Instruments with Integrated Electrocautery", Sep. 9, 2002.

13. International Patent Application Publication No. WO 2016/127178 A1, Colquhoun, S., "Electrocautery Device", Aug. 11, 2016.

14. U.S. Patent Application Publication No. US 2016/0228176 A1, Colquhoun, S., "Electrocautery Device", Aug. 11, 2006.

Unless clearly specified to the contrary, there is no requirement for any particular described or illustrated activity or element, any particular sequence or such activities, any particular size, speed, material, duration, contour, dimension or frequency, or any particularly interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. It should be appreciated that aspects of the present invention may have a variety of sizes, contours, shapes, compositions and materials as desired or required.

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the following claims, including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

We claim:

1. A port apparatus for use for providing electrocautery for surgery on a site of a subject, said device comprising:
an expandable sheath device, wherein said expandable sheath device having a distal portion and a proximal portion separated longitudinally from one another, wherein said expandable sheath has a tip at said distal portion;
a diode disposed on said distal portion of said expandable sheath device, wherein position of said diode is longitudinally spaced from said tip of said expandable sheath toward said proximal portion of said expandable sheath;
an electro-surgical terminal disposed on said proximal portion of said expandable sheath device;
a wire disposed longitudinally on said expandable sheath device, wherein said wire is in communication with said diode and said electro-surgical terminal;
a trocar device, wherein said expandable sheath device is configured to receive said trocar device that extends longitudinally through said expandable sheath;
a dilator, wherein said trocar device is configured to receive said dilator that extends longitudinally through said trocar device; and
said expandable sheath is configured to expand radially outward into an expanded state upon receiving said trocar device that has a radius larger than the radius of said expandable sheath in an unexpanded state.

2. The port apparatus of claim 1, wherein said apparatus is configured for use as a laparoscopic or thoracoscopic port for laparoscopic or thoracoscopic surgery, respectively.

3. The port apparatus of claim 1, wherein:
said trocar device is configured to receive a needle that extends longitudinally through said trocar device.

\* \* \* \* \*